United States Patent
Schütze et al.

(10) Patent No.: US 12,310,873 B2
(45) Date of Patent: May 27, 2025

(54) FLEXIBLE SUPPORT ELEMENT FOR AN ORTHOSIS

(71) Applicant: Bauerfeind AG, Zeulenroda-Triebes (DE)

(72) Inventors: Frank Schütze, Langenwolschendorf (DE); Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 228 days.

(21) Appl. No.: 16/083,271

(22) PCT Filed: Mar. 7, 2017

(86) PCT No.: PCT/EP2017/055242
§ 371 (c)(1),
(2) Date: Sep. 7, 2018

(87) PCT Pub. No.: WO2017/153364
PCT Pub. Date: Sep. 14, 2017

(65) Prior Publication Data
US 2019/0091054 A1    Mar. 28, 2019

(30) Foreign Application Priority Data

Mar. 8, 2016  (DE) .................. 10 2016 203 780.3

(51) Int. Cl.
| | |
|---|---|
| *A61F 5/00* | (2006.01) |
| *A61F 5/01* | (2006.01) |
| *A61F 5/02* | (2006.01) |

(52) U.S. Cl.
CPC .............. *A61F 5/0123* (2013.01); *A61F 5/01* (2013.01); *A61F 5/02* (2013.01); *A61F 2005/0141* (2013.01)

(58) Field of Classification Search
CPC ............ A41D 13/0531; A41D 13/0153; A41D 13/05; A61F 5/026; A61F 5/028;
(Continued)

(56) References Cited

U.S. PATENT DOCUMENTS 1,316,915 A * 9/1919 Meyer .................... A61F 5/028
602/19
4,144,881 A    3/1979 Chappell
(Continued)

FOREIGN PATENT DOCUMENTS

| DE | 10 2010 005939 A1 | 7/2011 |
|---|---|---|
| DE | 102011076843 A1 | 12/2012 |

(Continued)

OTHER PUBLICATIONS

Mariam-Webster definition for 'orthosis' (Year: 2021).*
(Continued)

*Primary Examiner* — Kim M Lewis
(74) *Attorney, Agent, or Firm* — George Likourezos; Carter, DeLuca & Farrell LLP

(57) ABSTRACT

The invention relates to a flexible support element for an orthosis, made of a link chain with several identical chain links, overlapping each other, firmly coupled in each case by a common bearing pin while limited by each other, which are pivotable to achieve a flexibility of the support element.

12 Claims, 10 Drawing Sheets

Figure 1:
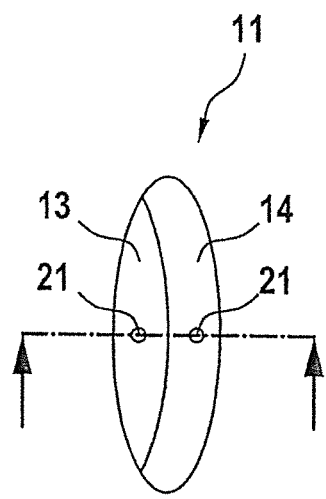

(58) Field of Classification Search
CPC .... A61F 5/0102; A61F 5/0123; A61F 5/0125; A61F 5/0127; A61F 2005/0141; A61F 2005/0155; A61F 2005/0165; A61F 2005/0169; A61F 5/01; A61F 5/02; A61F 5/022; A61F 5/024; A61F 5/00; A61F 5/055
USPC .............................................. 602/19, 23, 26
See application file for complete search history.

(56) References Cited

U.S. PATENT DOCUMENTS

| | | | | |
|---|---|---|---|---|
| 4,573,455 | A * | 3/1986 | Hoy | A61F 5/0123 602/16 |
| 5,400,801 | A * | 3/1995 | Archer, III | A41D 13/0153 2/92 |
| 5,840,051 | A * | 11/1998 | Towsley | A61F 5/055 602/19 |
| 6,296,644 | B1 * | 10/2001 | Saurat | A61B 17/7055 606/256 |
| 9,232,825 | B2 * | 1/2016 | Bencini | A41D 13/0531 |
| 10,072,794 | B2 * | 9/2018 | Koch | F16M 13/022 |
| 2003/0208147 | A1 * | 11/2003 | Reinecke | A61F 5/024 602/19 |
| 2004/0193085 | A1 | 9/2004 | Mazzarolo | |
| 2006/0211967 | A1 | 9/2006 | Reynolds et al. | |
| 2008/0319363 | A1 * | 12/2008 | Pansiera | A61F 5/0123 602/16 |
| 2009/0216167 | A1 * | 8/2009 | Harris | A61F 5/0127 36/89 |
| 2010/0263111 | A1 * | 10/2010 | Leatt | A41D 13/0531 2/467 |
| 2015/0209215 | A1 * | 7/2015 | Lee | A61H 3/008 623/27 |
| 2017/0049177 | A1 * | 2/2017 | Margetis | A42B 3/046 |
| 2017/0196722 | A1 * | 7/2017 | Murdock | A61F 5/028 |

FOREIGN PATENT DOCUMENTS

| | | |
|---|---|---|
| EP | 0212206 A1 | 3/1987 |
| EP | 2923686 A2 | 9/2015 |

OTHER PUBLICATIONS

Britannica, The Editors of Encyclopaedia. "elasticity". Encyclopedia Britannica, May 6, 2021, https://www.britannica.com/science/elasticity-physics. Accessed Aug. 11, 2022. (Year: 2022).*
International Search Report corresponding to Appln. No. PCT/EP2017/055242 dated Apr. 24, 2017 (3 pages).
Written Opinion (English translation) of PCT/EP2017/055242 dated Apr. 24, 2017.

* cited by examiner

FLEXIBLE SUPPORT ELEMENT FOR AN ORTHOSIS

The invention relates to a flexible support element for an orthosis, made of a link chain with several identical chain links, overlapping each other, firmly coupled in each case by a common bearing pin while limited by each other, which are pivotable to achieve a flexibility of the support element.

Orthoses serve as medical aids for stabilizing, relieving stress, immobilization and, in particular, for guiding or correcting a patient's limbs and shoulder, pelvis and spine. Mechanical stabilization and guiding or correction is achieved in particular by mechanically rigid stabilizing elements in the orthosis, which are brought into firm mechanical contact with the body using suitable bandages and/or belt elements, such that supporting forces can be absorbed or correction forces can be exerted. These are so-called hard-frame orthoses for limb joints, for example knee joint orthoses, in which joint rails, especially on both sides of the joint, bridge the joint and are thus mechanically firmly connected to the limb in order to absorb supporting forces and to support and/or correct the movement of the joint. The joint rails are firmly connected to the limb by suitable means such as bandages and straps distal and proximal to the joint; in the case of a knee brace, this occurs via frames mounted on the lower leg and thigh. In this case, the bilateral joint rails are mechanically firmly connected to each another via "bridges", so as to form the rigid hard frame for the orthosis. Similar constructions are well-known for elbow, wrist and ankle orthoses.

A disadvantage of commonplace hard-frame orthoses, especially knee-joint orthoses, are specifically these rigid bridges between the two lateral joint rails. On the one hand, they must be designed to be mechanically strong in order to link the two joint rails to each other in a useful way. However, known constructions cannot be adapted to the contour of the limb, to which they must be mechanically firmly connected, with sufficient precision. It appears, however, that, depending on the movement phase and the load on the limb, the external shape and circumference of the limb changes locally, especially because of the associated muscle deformation. The problem therefore arises that such a hard frame cannot be sufficiently maintained during movement, and slips out of the desired position, that is, it "migrates", and therefore the supporting effect, and also comfort, can be significantly impaired. Previous solutions to this problem suggest stronger mechanical tensions or strains between the hard frame and the limb. This should then be achieved by additional straps that are firmly tightened and/or by anti-slip coatings on the hard frame, on the side facing the limb. As a result, however, the wearing comfort of a hard frame orthosis and, thus, the patient's acceptance, are reduced. For example, this may cause the patient to no longer completely carry out the therapeutically-required joint movement and to assume a protective posture, which can work against the treatment. It is desirable to provide a hard-frame orthosis that fits firmly and securely to the patient's body during each phase of movement.

Another disadvantage of such hard frames with rigid coupling bridges between the joint rails is that they are not readily adaptable to different body sizes, i.e. most notably, the circumferences of the limb. The circumference of the limb may change, especially during the course of therapy, for example, during muscle-building rehabilitation; a rigid hard frame will not fit anymore. A hard frame is desirable for a supporting or correcting orthosis which can be flexibly adapted to the circumference of the limb.

Back braces for support and/or correction of the pelvis and/or spine usually contain rigid support elements or support rails that run laterally or, more commonly, centrally along the spine. These are pressed against the pelvis and/or spine, in particular by straps or bandages, in order to provide a supportive or corrective effect on the pelvis and/or spine by the appropriate application of force. A disadvantage of commonplace back braces or spinal orthoses is that these rigid support elements inadequately follow the patient's movements. However, a mechanical support and correction effect should be achieved, which is why these support elements must be mechanically strong and must be able to absorb forces. It appears, however, that higher therapeutic success can be found especially in targeted guided movement, than in a very rigid frame, which does not allow significant movement because of its mechanical strength. Conventional "straight" support rails, especially for patients with scoliosis, only follow the lordosis and/or kyphosis of the spine, and are not sufficiently adaptable to additional lateral curvatures of the spine. Therefore, pelvic and spinal orthoses are desirable where mechanically strong support elements that impart the support effect are designed so that they can partially or largely follow the patient's movement, but still provide mechanical support and limit unwanted movements.

The present invention was therefore based on the technical problem of developing mechanically rigid support elements of orthoses so that they allow a degree of flexibility and adaptability, but at the same time are mechanically strong and able to absorb forces to provide the desired mechanical support effect. One aspect is that they can replace conventional rigid support or coupling elements in known orthosis constructions.

The technical problem is completely solved by providing a flexible support band for an orthosis, which is constructed from a flat link chain, where a series of identical flat components are connected together. In this case, each component spatially and physically overlaps the adjacent component and is firmly coupled. In this case, the components are specially made of a mechanically strong material, specifically a plastic, metal or a composite of materials (e.g. a sandwich or inserts), and are therefore largely mechanically rigid in themselves.

In each case, a coupling or bearing pin provides firm coupling. It is notably aligned substantially perpendicular to the flat components. The linked elements can pivot against each other in their common axis with this bearing pin. According to the invention, the respective connected links of the chain overlap, that is, they overlap each other on the surface. According to the invention, shoulders are formed at the overlapping portions of the components, which the respective adjacent component physically supports, whereby the respective pivoting of the components limits one another on the axis of the bearing pin.

Thus, a novel semi-flexible support element provided in the form of a flat band is created, which is sufficiently mechanically strong, and is tensile and crush-resistant especially in its longitudinal orientation, however, bendable to a certain extent sideways and thus flexible from its longitudinal orientation out of a straight extension. This bendability and flexibility is made possible by the pivoting capacity of the links of the chain with each other on the axis of the respective coupling bearing pin. This pivoting, and thus the bending and flexibility in the longitudinal direction of the chain, is however limited by the mutual spatial limitation of the components on the shoulders of the adjacent components, according to the invention.

There is a basically flat band or rail-shaped structure under a support band that can serve as part of an orthosis or a solid orthosis frame as a solid support element or as an additional element or joint element connecting the bridge element.

A first object of the invention is therefore a flexible support band for an orthosis, which contains a flat link chain of several, in particular, identical, flat members, where every first member physically passes over a second adjacent component at over/under-crossing sections of the members respectively, and these members are firmly coupled to each other by a perpendicular pin, whereby the members are pivotable about the axis of this common pin with respect to each other. A shoulder is formed at an overlapping (under-crossing and over-crossing) link portion, which forms an end stop to limit this pivoting.

In a preferred configuration, the bearing pin is formed on the under-crossing link portion of the first member and a corresponding bushing or recess for receiving the pivot is formed on the over-crossing section of the component of the adjacent second member. The bearing pin engages in the bearing bush in this configuration, in order to securely couple the member.

In a special configuration, the bearing pin has a thickened head when compared to the diameter of the bearing bush, which the bearing pin is to engage with, which allows close-fit engaging of the bearing pin into the bearing bush of the adjacent component and prevents the bearing pin from slipping out of from the bearing bush against resistance.

Alternatively or additionally, the chain links also have additional snap-in noses for preventing the slipping or decoupling of the members from each other, which are engaged in corresponding recesses of the adjacent components, in order to prevent one component lifting out of one member out of the adjacent chain link.

In another configuration, the bearing pin is designed as a screw or rivet. In a specific configuration of this, each of the two members to be coupled are provided with recesses in the form of bearing bushing, where the members are each coupled by a separate rivet or bolt, which is driven by both bushings, or a separate screw which is screwed into the same place. Rivets or screws are secured in a conventional manner: rivets by specific two-sided rivet heads, and screws in particular with a screw head and a bearing bushing designed with a thread.

In all configurations, the bearing pin and the bearing bushing are preferably each centered with respect to the longitudinal alignment of the link chain, i.e. positioned on the center line; preferably, the bearing pin and bearing bushing are positioned off-center (eccentric) to the transverse axis of each link on the component.

It is especially intended that at least one of the shoulders which form the end stop should have an elastic element to dampen impact. Such an elastic element is preferably an elastic material applied to the rigid material of the member, in particular an elastic polymer in the form of an element superimposed or inserted into the shoulder wall or in the manner of a layer of rubber coating. In an alternative configuration, there is an functional element formed by a targeted material recess or a milled groove in the rigid material of the member, i.e. a elastic, flexibly-resilient functional element.

This invention's support band is constructed of a series of identical members. The invention thus advantageously allows individual members of the chain to be removed or added in order to adapt the length of the support element or the coupling bridge to the anatomical conditions and/or the respective therapeutic objective. The links can be reversibly separated from each other or re-assembled by an orthopedic technician through a specially designed locking mechanism in the coupling.

The link chain as a component of the support band according to the invention preferably has differently shaped end members at each end, which are specifically designed to mechanically link the members of the link chain, and thus the support band, to the other elements of the orthosis, in particular other hard frame sections, hinge rails or support frames. In a hard frame orthosis with a joint-crossing hard-frame system, the end member of the link chain is used in each case for coupling the link chain with a joint rail extending to the joint, and in particular for the respective coupling of two joint rails running on either side of the joint. In this specific configuration, the support band according to the invention serves functionally as a mechanically-fixed coupling bridge between the two lateral hinge rails. Advantageously, the flexible support band of this invention allows an anatomically correct, and also adaptable form to the distal and/or proximal portion of the limb. The support band shows flexibility and mobility and can adequately follow the anatomical contour of the limb during movement, and as such always fits on the limb well. In addition, the coupling bridge thus formed between the two lateral joint rails allows them to move in parallel with each other, allowing dynamic positioning of the joint rail over the body joint when in movement, improving the support function in each phase of movement; the positioning is therefore largely self-adjusting. An undesirable migration of the orthosis can be prevented.

In a preferred variant, the end link of the link chain is connected to the hinge rail by one or more eccentric elements, for example via eccentric screws. As a result, additional adjustment of the angle of the end component, and the connected support band, to the link chain is made possible. An improved anatomical shaping of the joint rail and hard frame can thus be achieved. This is especially advantageous if a multi-axial or self-locating joint is used in the joint rail.

Especially in the configuration as a bridge encompassing (coupling) the limb in a hard-frame orthosis, preferential use of a symmetrical structure of the link chain is intended. For this purpose, the link chain preferably has a preferably centrally positioned specially designed center member, which has a substantially mirror-image symmetrical structure. In particular, corresponding over-crossing portions of members are formed on both sides of the middle component so as to overlap with the corresponding under-crossing member portions of the members which can be coupled thereto on both sides, whereby the alignment of the chain members within the link chain are reversed at this center link.

The uni-axial coupling of the components with each other, according to the invention, allows pivoting of the components within the primary plane of the flat support band to the longitudinal axis, and it is additionally intended in preferred configurations that the components are bendable with respect to each other in the longitudinal axis of the support band, and also perpendicular to the primary plane of the flat support band are in order to guide the flat support band in an arc. For this purpose, in a first configuration, it is preferably intended that the components each have a certain inherent elasticity. This can be achieved by selecting the material of the member, through local material dilutions, but also by inherent elasticity alone of the bearing pivot provided for coupling the components. In an alternative or additional variant, the bearing bush of the respectively adjacent component is sized and shaped such that a bearing pin is not guided there without play, but can tilt in the bearing bush (tilting play). Thus, this allows for a tilting movement of the components adjacent to each other within certain limits. This advantageously makes it possible to put the support band, which is in itself flat, into an arched shape, in particular in order to adapt it to the contour of a limb. In other configurations of the support band according to the invention, the members are coupled as play-free in this respect, in order to provide a supporting effect in this area. This is especially for use in spinal or back braces, for example, if a kyphosis or lordosis is to be supported, but the support band according to the invention should allow lateral movement of the spine or scoliosis. In another configuration, sections of play-free, tilt-free coupling and sections with tilt play and/or flexible members are formed in the support band along the link chain in order to make the support effect adaptable to the anatomical conditions and/or the treatment objectives. In this variant, members with play-free couplings and other members with couplings with tilt play and/or flexible members are provided, which can each be joined together in the manner of a kit in order to build these sections onto the link chain. Through the coupling's specially designed latching mechanism, the various members can be reversibly separated and put together or replaced by an orthopedic technician.

The subject matter of the invention is also a hard-frame joint orthosis, which in particular has two opposing joint rails which run along the body joint, wherein the joint rails are coupled together via the flexible support band of this invention, proximally and/or distally to the joint. In one of its particular configurations, the end components are configured such that therein the joint rails are guided in each case with capacity for displacement. In this configuration, the end members serve as a receiving element of the joint rails. They preferably serve as a point of articulation of straps for mounting the respective limb sections, for example a thigh and/or a lower leg. Such joint orthoses are knee joint orthoses, elbow orthoses, wrist orthoses, finger joint orthoses, ankle, ankle orthoses, toe and back orthoses, and similar.

Finally, another object of the invention is a back brace, specifically for supporting the spine, whereby the flexible support band of this invention is included as a support component for supporting the spine.

The invention is explained in more detail by the following exemplary embodiments, without them being restrictive.

FIG. 1 shows a single member 11 of the link chain according to the invention.

Figure 2:
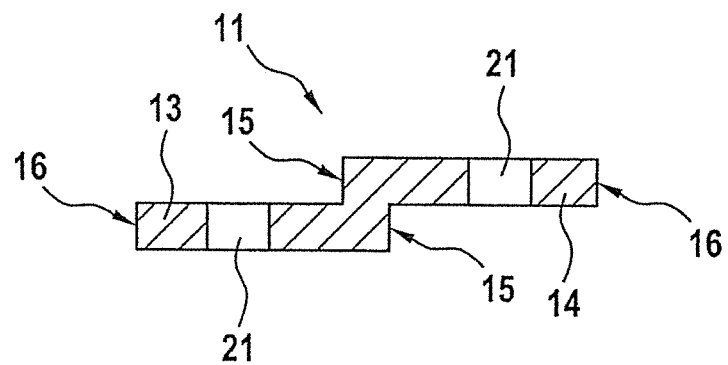

FIG. 2 shows a sectional view of the intersecting line shown in FIG. 1: The member 11 has a flat body. The configuration shown here has eccentric recesses 21 on both sides which are formed as bearing bushes for receiving bearing bolt or pin 20 for coupling several members together. Each member 11 has an under-crossing portion 13 and an adjacent member cross-over section 14. On the member 11 each shoulder surface or edge 15, 16 are formed, which serve as end stops for this pivoting when these members are coupled together and these members pivot on an axis formed by bushing 21 and bearing pin 20.

Figure 3:
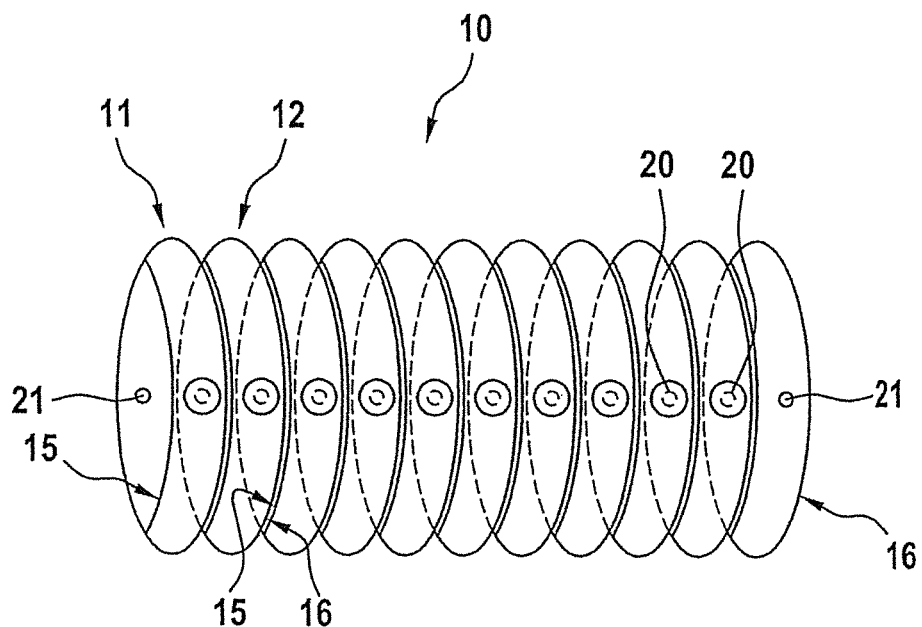

FIG. 3 shows the plan view of a section of a link chain 10 with members 11, 12 coupled together according to the invention.

Figure 4:
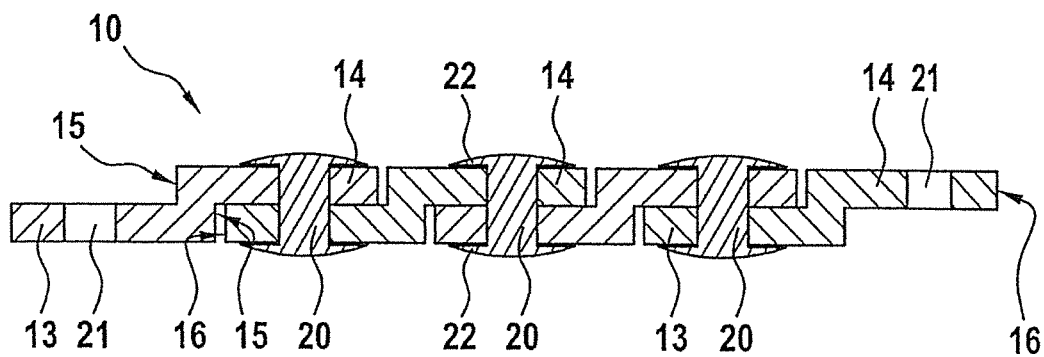

FIG. 4 shows a sectional view thereof on the intersecting line shown in FIG. 3: A first component 11 is in each case coupled to a component 12 adjacent to it. When the members 11, 12 are coupled together, the over-crossing and under-crossing sections 13, 14 of the respective members overlap, such that an over-crossing section 14 of one member 14 is in flat-surface contact with an under-crossing section 13 of the adjacent link 12. Coupling is achieved by a separate bearing pin 20, which is guided here by two bearing bushes 21 of adjacent members 11,12 and couples these in this way. The bearing pin 20 is designed here as a rivet with bilateral rivet heads 22. The shoulders 15, 16 formed at the portions and outer edges of the respective links 11, 12 are in physical contact with each other as the links pivot.

Figure 5:
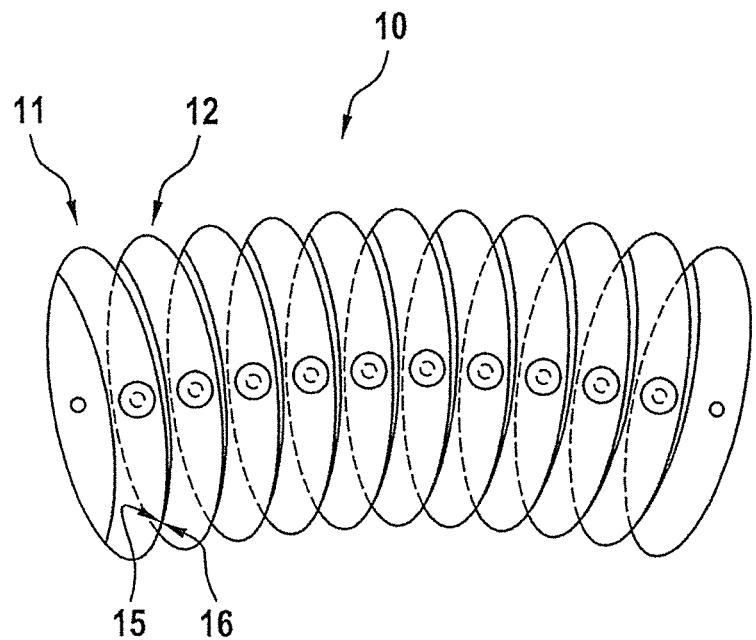

FIG. 5 shows the link chain 10 of FIG. 3 when the links are pivoted against one another: The shoulders 16 and 15 of adjacent components abut each other in each case to limit the pivoting.

Figure 6:
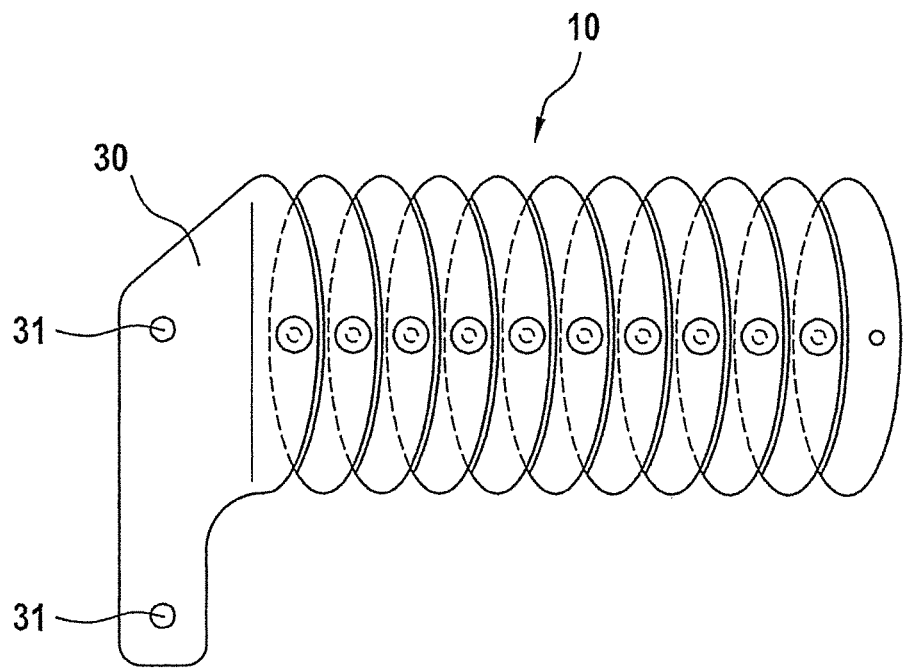

FIG. 6 shows the plan view of an end section of the link chain 10 according to the invention with a special end link 30 for the mechanical coupling of the link chain with the remaining components of an orthosis, which comprises suitable material 31, here: Recesses for inclusion of screws or rivets. A bearing pin 20 or a bearing bush 21 is also formed at the end component 30 for the purpose of coupling with the first member 11 of the further link chain of identical components. The end member has a over-crossing portion 34 in the illustrated configuration which overlaps with an under-crossing 13 of the first member 11 when coupled.

Figure 7:
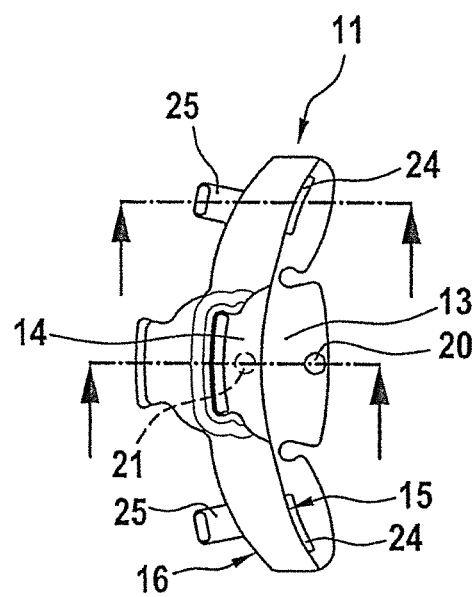

FIG. 7 shows a further configuration of a single chain member 11 of a link chain as per the invention.

Figure 8:
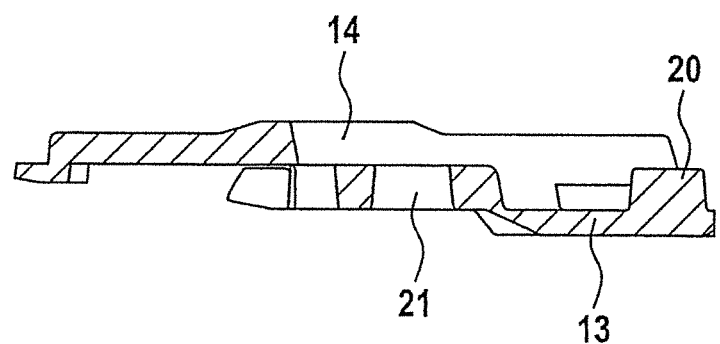
Figure 9:
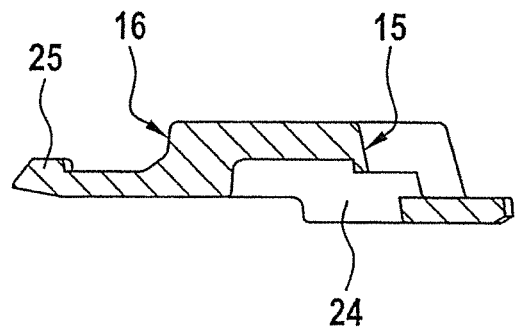

FIGS. 8 and 9 respectively show sectional views of this component at the intersecting lines indicated in FIG. 7: FIG. 8 shows the central section; FIG. 9 shows the section in the region of the snap-in nose 25. Each member 11 has at least one over-crossing portion 14 and at least under-crossing portion 13. On the upper-crossing portion 13, an integrated bearing pin 20 is provided in the illustrated configuration, which can engage a bearing bush 21 of an adjacent component to couple the members. The bearing pin 20 is formed integrally with the member 11. In the illustrated configuration, each component has additional snap-in noses 25 that can be engaged with recesses 24 of an adjacent component to prevent the components detaching out from each other from the bearing sleeve 21, while optionally preventing undesirable excessive torsion of the link chain along its longitudinal axis.

Figure 10:
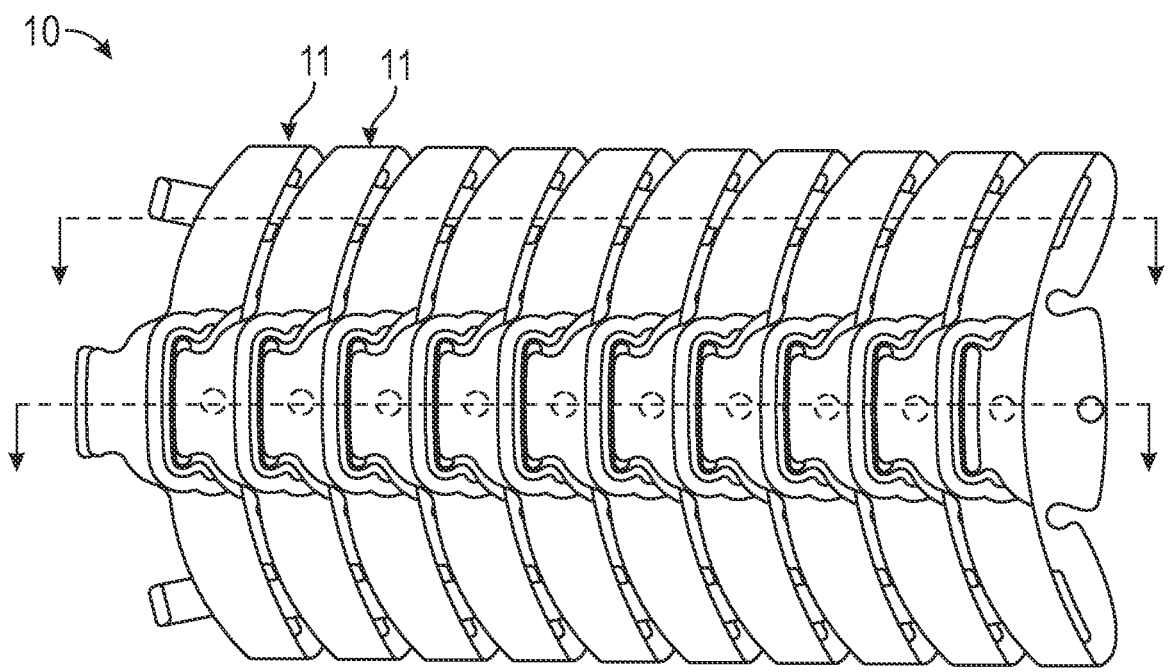

FIG. 10 shows the plan view of a section of a link chain 10 with members 11, 12 coupled together according to the invention.

Figure 11:
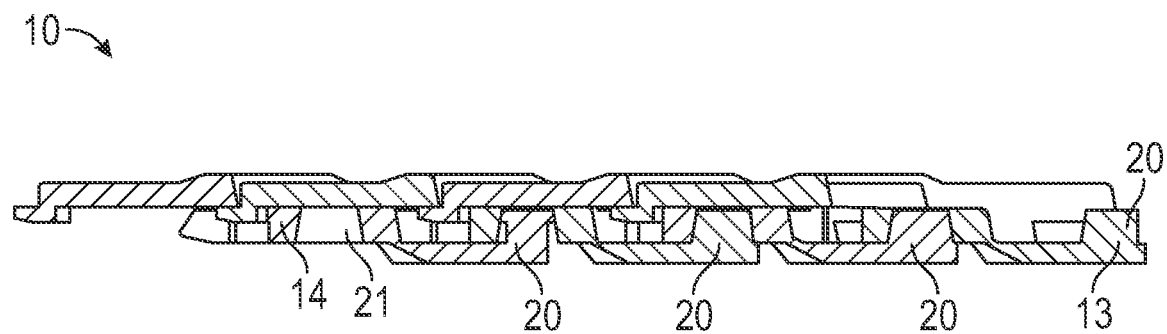
Figure 12:
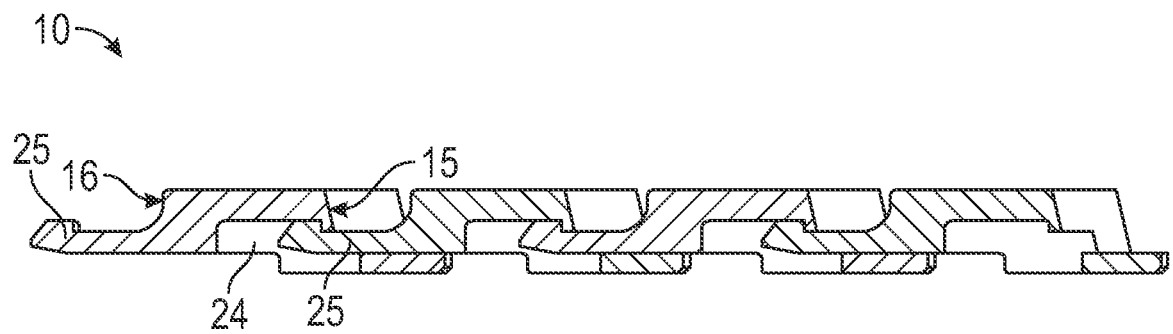

FIGS. 11 and 12 respectively show sectional views of this component at the intersecting lines indicated in FIG. 7: FIG. 11 shows the central section; FIG. 12 shows the section in the region of the snap-in noses 25. A first component 11 is in each case coupled to a component 12 adjacent to it. When the members 11, 12 are coupled together, the over- and under-crossing sections 13, 14 of the respective members overlap. The shoulders 15, 16 formed on the sections and outer edges of the respective components 11, 12 are in physical contact when the links are pivoted toward one another.

Figure 13:
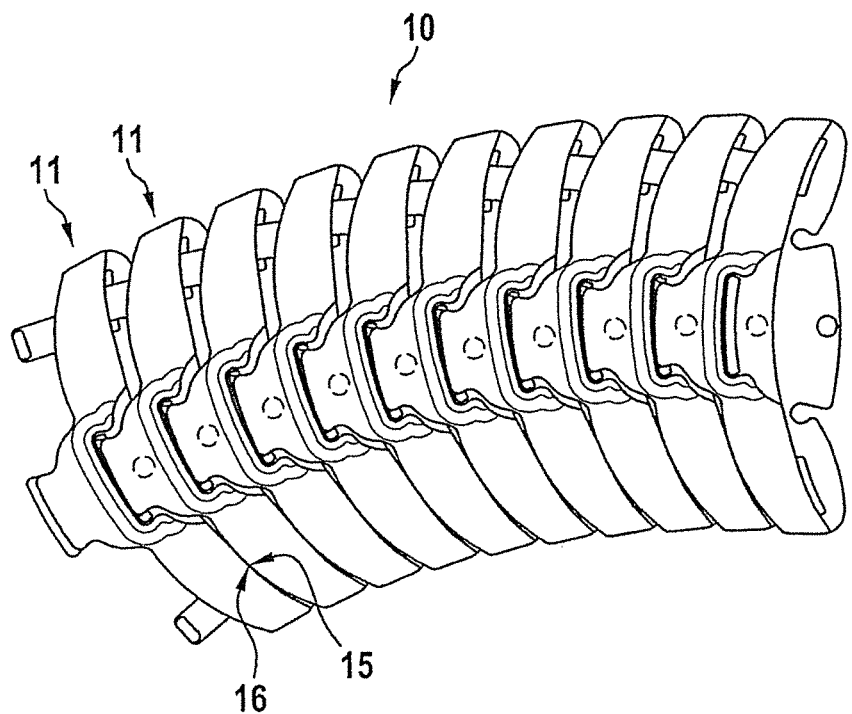

FIG. 13 shows the link chain 10 of FIG. 10 when the links are pivoted against one another: The shoulders 16 and 15 of adjacent components abut each other in each case to limit the pivoting.

Figure 14:
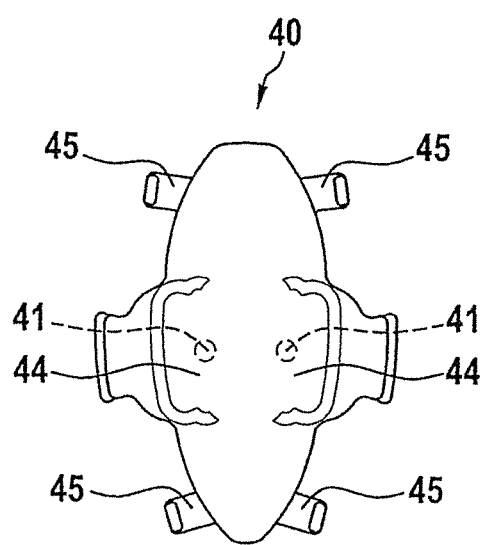

FIG. 14 shows a special middle link 40 of the link chain 10 as per the invention, which has over-crossing sections 44 on both sides similar to the over-crossing sections 14 of a single identical link 11 and bearing bushes 41, identical to the bearing bushes 21 of the single identical member 11. The middle piece 40 serves to make the alignment of the identical links 11 in the chain symmetrical on either side of the middle piece 40. In the illustrated configuration, snap-in noses 45 are additionally formed, which can engage in corresponding recesses 24 of the identical coupleable members 11 on both sides.

Figure 15:
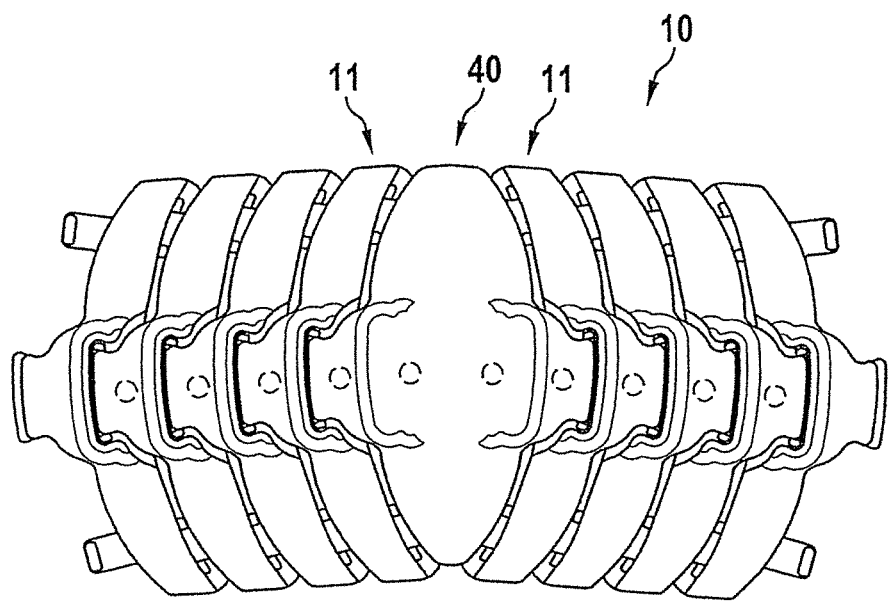
Figure 16:
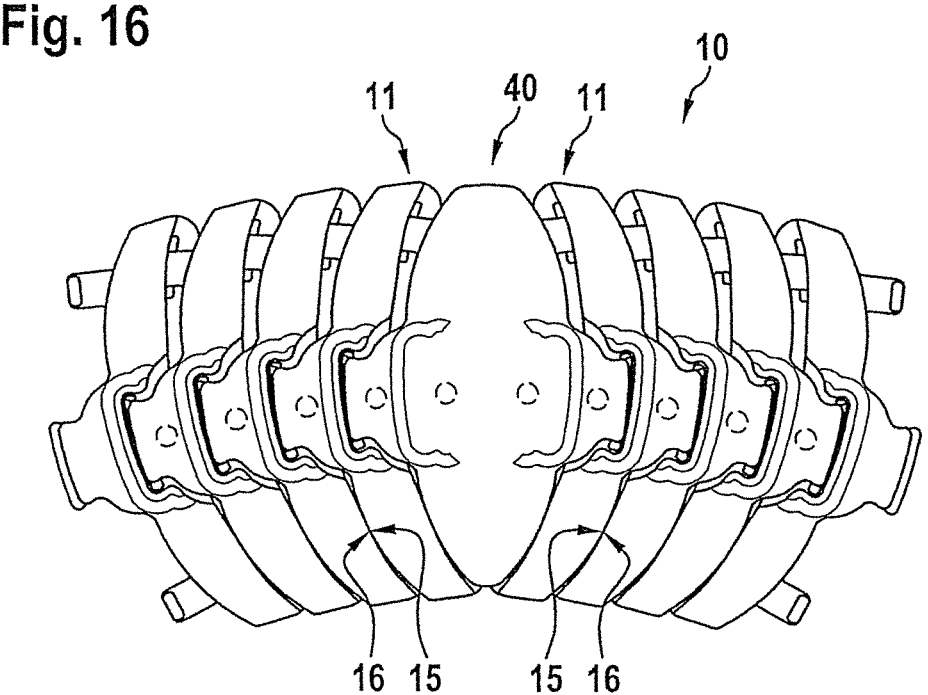

FIGS. 15 and 16 each show plan views of a section of a configuration of the link chain 10 according to the invention, which are constructed from identical links 11 and a central section 40 acting to make the set-up symmetrical. FIG. 15 shows this link chain 10 in an elongated arrangement; FIG. 16 shows the link chain upon pivoting of the individual components respectively in the pivot axes formed by bearing pin 20 and bearing bush 21 to the end stop of the pivoting of the respective shoulders 16, 15 of the members.

Figure 17:
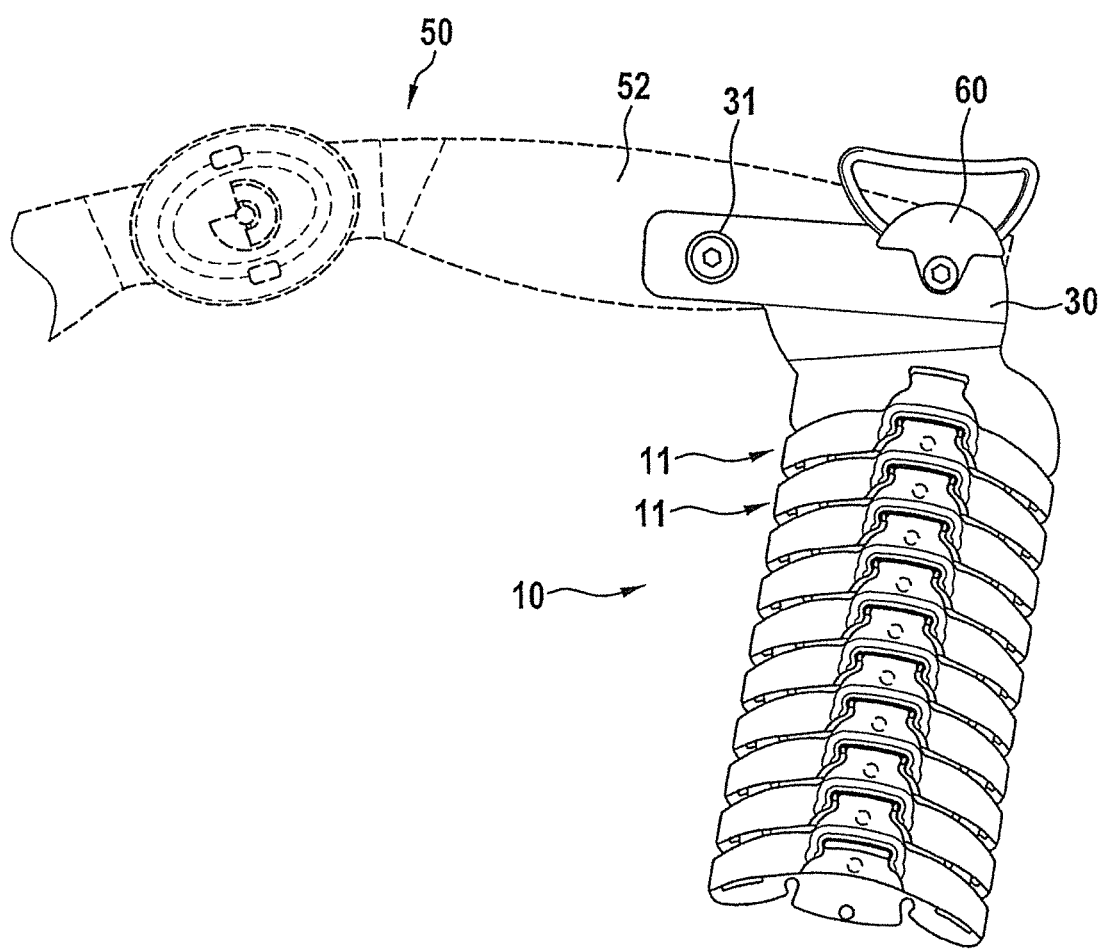

FIG. 17 is a schematic representation of a detail of a hard-frame knee-joint orthosis having a portion of the support band made of a link chain 10 according to the invention with identical links 11 and end link 30. In this configuration, the joint rails 50 are screwed with a joint leg 52 on the specifically designed end member 30 in recesses 31. Furthermore, optionally removable tabs 60 for receiving and fixing straps are formed on the end component.

Figure 18:
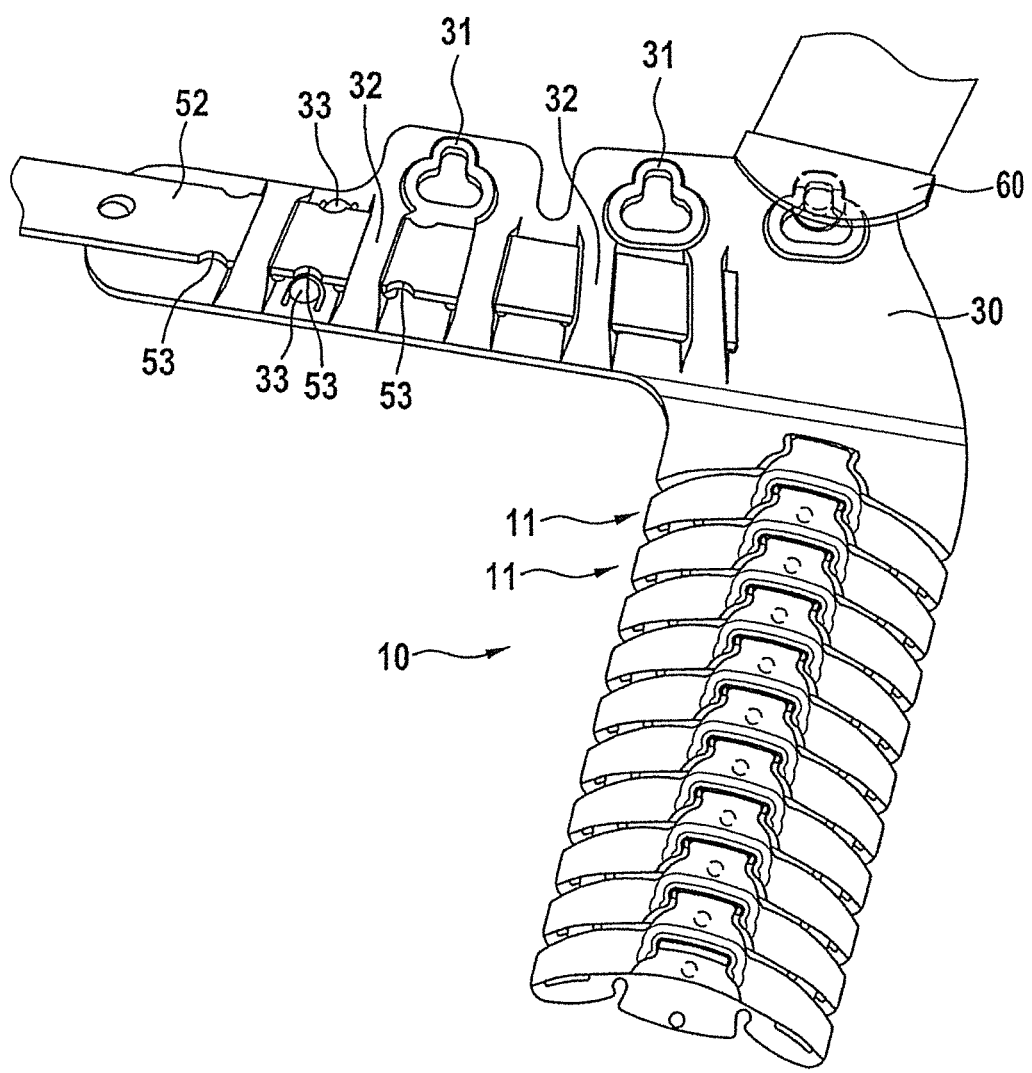

FIG. 18 is a schematic representation of a detail of a hard-frame knee-joint orthosis having a portion of the support band made of a link chain 10 according to the invention with identical links 11 and end link 30. In this configuration, the joint leg 52 of the joint rail of the orthosis is guided in the specifically designed end member 30 in guide loops 32 and held so that it fits the shape. To adjust the effective length of the joint rail, the joint leg 52 is supported by, and can be moved around within the end member and can be fixed to moveable and locking elements 33 of the end component 30 which can firmly engage in notches 53 of the joint leg 52. Furthermore, one or more removable tabs 60 for receiving and fixing straps are optionally formed on the end component. In the illustrated configuration, the tabs 60 snap into specifically shaped recesses 31 on the end component 30 of the support component.

Figure 19:
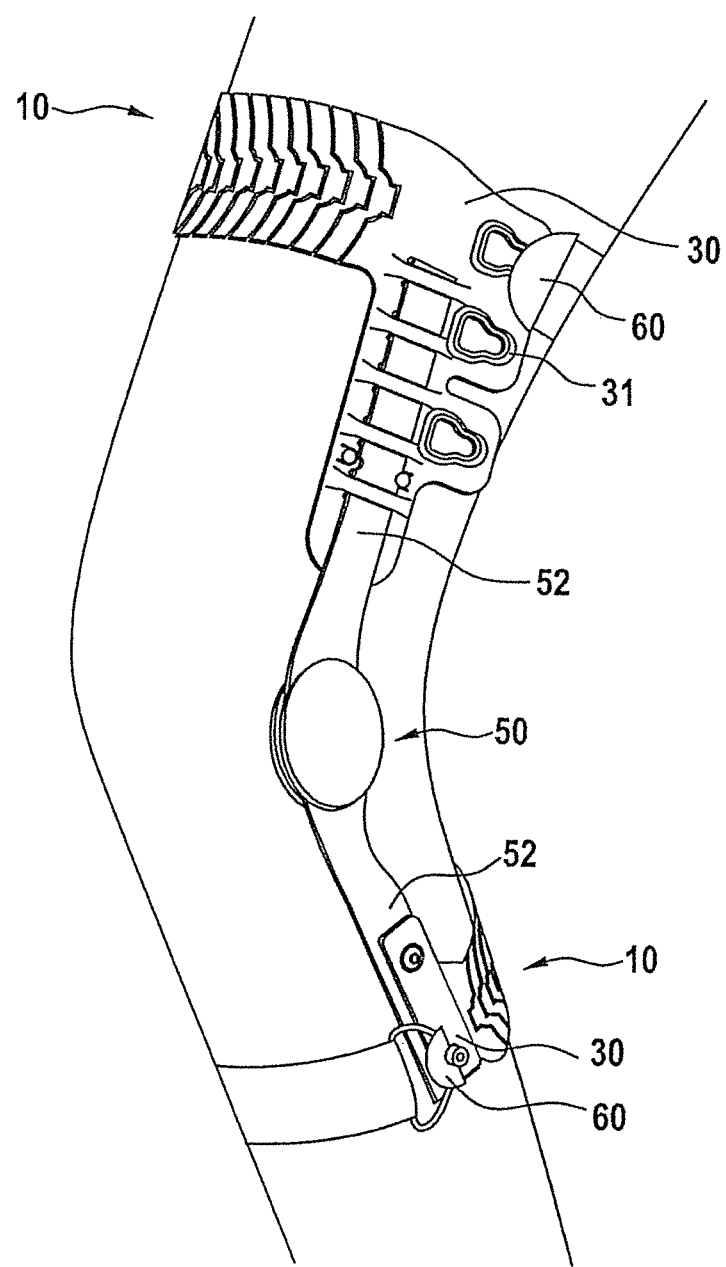

FIG. 19 is a schematic perspective view of a configuration of a hard-frame joint orthosis according to the invention, which has the flexible support bands according to the invention as coupling bridges between the two joint rails.

The invention claimed is:

1. A flexible support band for an orthosis, comprising:
a link chain having several identical members, each having a first member with an adjacent second member in respective over-crossing and under-crossing link sections physically overlapping one another, the first member and the adjacent second member tightly coupled to a bearing pin perpendicular to the first and adjacent second members about an axis of the bearing pin being pivotable against each other,
wherein shoulders of over-crossing link sections form an end stop to limit pivoting of the first and adjacent second members about the axis of the bearing pin, wherein the shoulders further include at least one of a material recess or a milled groove,
wherein the bearing pin is a protrusion integrally formed on the under-crossing link section of the first member and a bearing bushing is integrally formed on a portion of the over-crossing link section of a second member section of the adjacent second member and the bearing pin engages the bearing bushing to couple the first and adjacent second members, wherein the bearing pin when engaged in the bearing bushing, is along a central longitudinal axis of the member, and
wherein each of the members include a pivoting capacity between each other on the axis of the bearing pin enabling bending and flexibility in a longitudinal direction of the link chain.

2. The flexible support band according to claim 1, wherein at least one of the shoulders has an elastic element to dampen impact.

3. The flexible support band according to claim 2, in which a flat link chain has an end component through which the flat link chain can be fixed to the orthosis.

4. The flexible support band according to claim 2, wherein a flat link chain comprises a center member having a symmetrically identical structure on both sides with over-crossing components.

5. The flexible support band according to claim 2, wherein the bearing pin has a head which is thickened relative to a diameter of the bearing bushing in order to block disengaging of the first and adjacent second members from each other.

6. The flexible support band according to claim 2, wherein the flexible support band is configured as part of a back orthosis containing the flexible support band for supporting the spine of a user.

7. The flexible support band according to claim 1, in which a flat link chain has an end component through which the flat link chain can be fixed to the orthosis.

8. The flexible support band according to claim 1, wherein a flat link chain comprises a center member having a symmetrically identical structure on both sides with over-crossing components.

9. The flexible support band according to claim 1, wherein the bearing pin has a head which is thickened relative to a diameter of the bearing bushing in order to block disengaging of the first and adjacent second members from each other.

10. The flexible support band according to claim 1, wherein the flexible support band is configured as part of a back orthosis containing the flexible support band for supporting the spine of a user.

11. A flexible support band for an orthosis, comprising:
a link chain having several identical members, each having a first member with an adjacent second member in respective over-crossing and under-crossing link sections physically overlapping one another, the first member and the adjacent second member tightly coupled to a bearing pin perpendicular to the first and adjacent second members about an axis of the bearing pin being pivotable against each other,
wherein shoulders of over-crossing link sections form an end stop to limit pivoting of the first and adjacent second members about the axis of the bearing pin,
wherein the bearing pin is a protrusion integrally formed on the under-crossing link section of the first member and a bearing bushing is integrally formed on a portion of the over-crossing link section of a second member section of the adjacent second member and the bearing pin engages the bearing bushing to couple the first and adjacent second members, wherein the bearing pin when engaged in the bearing bushing, is along a central longitudinal axis of the member, and
wherein each of the members include a pivoting capacity between each other on the axis of the bearing pin enabling bending and flexibility in a longitudinal direction of a flat link chain,
wherein each of the first members includes a snap-in nose that is configured to engage with a recess of the adjacent second member to prevent the respective first member and second member from disengaging from each other and further configured to prevent torsion of the flat link chain along a longitudinal axis of the flat link chain, wherein the snap-in nose is located along each peripheral side of the flat member.

12. A flexible support band for an orthosis, comprising:

a flat link chain having several identical flat members, each having a first member with an adjacent second member in respective over-crossing and under-crossing link sections physically overlapping one another, the first member and the adjacent second member tightly coupled to a bearing pin perpendicular to the first and adjacent second members about an axis of the bearing pin being pivotable against each other, wherein shoulders of over-crossing link sections form an end stop to limit pivoting of the first and adjacent second members about the axis of the bearing pin, wherein the bearing pin is a protrusion integrally formed on the under-crossing link section of the first member and a bearing bushing is integrally formed on a portion of the over-crossing link section of a second member section of the adjacent second member and the bearing pin engages the bearing bushing to couple the first and adjacent second members, wherein the bearing pin when engaged in the bearing bushing, is along a central longitudinal axis of the flat member, wherein the bearing pin is located approximately in the middle of each member, and wherein each member is configured to pivot around the bearing pin location, and wherein each of the members include a pivoting capacity between each other on the axis of the bearing pin enabling bending and flexibility in a longitudinal direction of the flat link chain.

* * * * *